United States Patent
Clayton et al.

(10) Patent No.: US 8,684,175 B2
(45) Date of Patent: Apr. 1, 2014

(54) METHOD FOR SHIPPING AND PROTECTING AN ENDOTRACHEAL TUBE WITH AN INFLATED CUFF

(75) Inventors: Jessica Clayton, Campbell, CA (US); Donald S. Nelson, San Ramon, CA (US); David Swedlow, Danville, CA (US); Joel Colburn, Walnut Creek, CA (US); Roger Mecca, Danville, CA (US)

(73) Assignee: Covidien LP, Mansfield, MA (US)

( * ) Notice: Subject to any disclaimer, the term of this patent is extended or adjusted under 35 U.S.C. 154(b) by 1502 days.

(21) Appl. No.: 11/526,156

(22) Filed: Sep. 22, 2006

(65) Prior Publication Data

US 2008/0073231 A1    Mar. 27, 2008

(51) Int. Cl.
*A61B 19/02* (2006.01)
*B65D 83/10* (2006.01)

(52) U.S. Cl.
USPC .......................................... 206/363; 206/438

(58) Field of Classification Search
USPC ......... 206/204, 438, 363, 364, 365, 366, 439, 206/440, 570, 828, 522
See application file for complete search history.

(56) References Cited

U.S. PATENT DOCUMENTS

| | | | |
|---|---|---|---|
| 2,927,584 A | 3/1960 | Wallace | |
| 3,259,235 A * | 7/1966 | Sowle | 206/497 |
| 3,547,257 A | 12/1970 | Armentrout | |
| 3,612,038 A * | 10/1971 | Halligan | 600/435 |
| 3,784,056 A | 1/1974 | Spruyt et al. | |
| 3,810,474 A | 5/1974 | Cross | |
| 3,822,238 A | 7/1974 | Blair et al. | |
| 3,975,350 A | 8/1976 | Hudgin et al. | |
| 4,216,860 A * | 8/1980 | Heimann | 206/370 |
| 4,248,236 A * | 2/1981 | Linder | 604/100.01 |
| 4,340,046 A | 7/1982 | Cox | |
| 4,366,901 A * | 1/1983 | Short | 206/210 |
| 4,569,344 A | 2/1986 | Palmer | |
| 4,610,357 A * | 9/1986 | Nakamura | 206/449 |
| 4,638,539 A | 1/1987 | Palmer | |
| 4,696,296 A | 9/1987 | Palmer | |
| 4,825,859 A | 5/1989 | Lambert | |
| 4,834,726 A | 5/1989 | Lambert | |
| 4,836,199 A | 6/1989 | Palmer | |
| 4,838,255 A | 6/1989 | Lambert | |
| 4,863,016 A * | 9/1989 | Fong et al. | 206/439 |
| 4,867,153 A | 9/1989 | Lorenzen et al. | |

(Continued)

FOREIGN PATENT DOCUMENTS

| | | |
|---|---|---|
| CA | 2353007 A1 | 6/2000 |
| DE | 19855521 A1 | 6/2000 |

(Continued)

OTHER PUBLICATIONS

Tecogel brochure page, Noveon Thermedics Polymer Products, Oct. 2003.

(Continued)

*Primary Examiner* — Andrew Perreault

(57) ABSTRACT

An inflatable cuff may be adapted to seal a patient's trachea when associated with an endotracheal tube. Packaging and transporting of these cuffs while inflated may provide for decreased wrinkles and thereby improved sealing of the trachea. Provided is a package for a medical device with an inflatable region, comprising a substantially non-stretchable region that substantially conforms to the shape of the inflatable region of the medical device when the inflatable region is inflated.

36 Claims, 8 Drawing Sheets

(56) References Cited

U.S. PATENT DOCUMENTS

| | | | |
|---|---|---|---|
| 4,872,579 A | 10/1989 | Palmer | |
| D305,603 S | 1/1990 | Nelson et al. | |
| 4,925,448 A * | 5/1990 | Bazaral | 604/171 |
| 4,927,412 A | 5/1990 | Menasche | |
| 4,938,741 A | 7/1990 | Lambert | |
| 4,963,313 A | 10/1990 | Noddin et al. | |
| 4,967,743 A | 11/1990 | Lambert | |
| 5,021,045 A | 6/1991 | Buckberg et al. | |
| 5,025,806 A | 6/1991 | Palmer et al. | |
| 5,029,580 A | 7/1991 | Radford et al. | |
| 5,038,920 A | 8/1991 | Nelson | |
| 5,060,646 A | 10/1991 | Page | |
| 5,065,754 A | 11/1991 | Jensen | |
| 5,074,840 A | 12/1991 | Yoon | |
| 5,098,379 A | 3/1992 | Conway et al. | |
| 5,103,816 A | 4/1992 | Kirschbaum et al. | |
| 5,105,942 A * | 4/1992 | van Veen et al. | 206/364 |
| 5,107,829 A | 4/1992 | Lambert | |
| 5,120,322 A | 6/1992 | Davis et al. | |
| 5,122,122 A | 6/1992 | Allgood | |
| 5,133,345 A | 7/1992 | Lambert | |
| 5,135,516 A | 8/1992 | Sahatjian et al. | |
| 5,137,671 A | 8/1992 | Conway et al. | |
| 5,158,569 A | 10/1992 | Strickland et al. | |
| 5,165,420 A | 11/1992 | Strickland | |
| 5,190,810 A | 3/1993 | Kirschbaum et al. | |
| 5,199,427 A | 4/1993 | Strickland | |
| 5,207,643 A | 5/1993 | Davis | |
| 5,215,522 A | 6/1993 | Page et al. | |
| 5,218,957 A | 6/1993 | Strickland | |
| 5,221,007 A | 6/1993 | Foos | |
| 5,230,332 A | 7/1993 | Strickland | |
| 5,233,979 A | 8/1993 | Strickland | |
| 5,246,012 A | 9/1993 | Strickland | |
| 5,250,070 A | 10/1993 | Parodi | |
| 5,261,896 A | 11/1993 | Conway et al. | |
| 5,263,478 A | 11/1993 | Davis | |
| 5,269,770 A | 12/1993 | Conway et al. | |
| 5,277,177 A | 1/1994 | Page et al. | |
| 5,290,585 A | 3/1994 | Elton | |
| 5,304,121 A | 4/1994 | Sahatjian | |
| 5,318,021 A * | 6/1994 | Alessi | 128/207.15 |
| 5,322,161 A * | 6/1994 | Shichman et al. | 206/204 |
| 5,331,027 A | 7/1994 | Whitbourne | |
| 5,351,830 A * | 10/1994 | Bender et al. | 206/522 |
| 5,360,402 A | 11/1994 | Conway et al. | |
| 5,370,656 A | 12/1994 | Shevel | |
| 5,370,889 A | 12/1994 | Conway et al. | |
| 5,374,261 A | 12/1994 | Yoon | |
| 5,392,787 A | 2/1995 | Yoon | |
| 5,397,302 A | 3/1995 | Weaver et al. | |
| 5,407,423 A | 4/1995 | Yoon | |
| 5,417,671 A | 5/1995 | Jackson | |
| 5,423,745 A | 6/1995 | Todd et al. | |
| 5,439,457 A | 8/1995 | Yoon | |
| 5,447,505 A | 9/1995 | Valentine et al. | |
| 5,451,204 A | 9/1995 | Yoon | |
| 5,466,231 A | 11/1995 | Cercone et al. | |
| 5,469,864 A | 11/1995 | Rosenblatt | |
| 5,482,740 A | 1/1996 | Conway et al. | |
| 5,484,426 A | 1/1996 | Yoon | |
| 5,487,730 A | 1/1996 | Maracadis et al. | |
| 5,494,029 A | 2/1996 | Lane et al. | |
| 5,501,669 A | 3/1996 | Conway et al. | |
| 5,507,284 A | 4/1996 | Daneshvar | |
| 5,509,899 A | 4/1996 | Fan et al. | |
| 5,524,642 A | 6/1996 | Rosenblatt | |
| 5,526,928 A * | 6/1996 | Yabe et al. | 206/364 |
| 5,545,132 A | 8/1996 | Fagan et al. | |
| 5,556,391 A | 9/1996 | Cercone et al. | |
| 5,593,718 A | 1/1997 | Conway et al. | |
| 5,599,292 A | 2/1997 | Yoon | |
| 5,599,299 A | 2/1997 | Weaver et al. | |
| 5,599,321 A | 2/1997 | Conway et al. | |
| 5,611,336 A | 3/1997 | Page et al. | |
| 5,613,950 A | 3/1997 | Yoon | |
| 5,649,902 A | 7/1997 | Yoon | |
| 5,655,657 A * | 8/1997 | Roshdy | 206/363 |
| 5,670,111 A | 9/1997 | Conway et al. | |
| 5,674,192 A | 10/1997 | Sahatjian et al. | |
| 5,693,014 A | 12/1997 | Abele et al. | |
| 5,694,922 A | 12/1997 | Palmer | |
| 5,700,239 A | 12/1997 | Yoon | |
| 5,715,815 A | 2/1998 | Lorenzen et al. | |
| 5,720,726 A | 2/1998 | Marcadis et al. | |
| 5,722,931 A | 3/1998 | Heaven | |
| 5,730,123 A | 3/1998 | Lorenzen | |
| 5,733,252 A | 3/1998 | Yoon | |
| 5,735,271 A | 4/1998 | Lorenzen et al. | |
| 5,749,358 A | 5/1998 | Good et al. | |
| 5,765,559 A | 6/1998 | Kim | |
| 5,765,682 A * | 6/1998 | Bley et al. | 206/363 |
| 5,769,882 A | 6/1998 | Fogarty et al. | |
| 5,810,786 A | 9/1998 | Jackson et al. | |
| 5,827,215 A | 10/1998 | Yoon | |
| 5,843,017 A | 12/1998 | Yoon | |
| 5,843,028 A | 12/1998 | Weaver et al. | |
| 5,843,060 A | 12/1998 | Cercone | |
| 5,843,089 A | 12/1998 | Sahatjian et al. | |
| 5,848,691 A * | 12/1998 | Morris et al. | 206/364 |
| 5,857,375 A | 1/1999 | Nelson et al. | |
| 5,868,719 A | 2/1999 | Tsukernik | |
| 5,951,597 A | 9/1999 | Westlund et al. | |
| 5,954,706 A | 9/1999 | Sahatjian | |
| 5,954,740 A | 9/1999 | Ravenscroft et al. | |
| 5,971,954 A | 10/1999 | Conway et al. | |
| 5,997,503 A | 12/1999 | Willis et al. | |
| 5,997,546 A | 12/1999 | Foster et al. | |
| 6,010,480 A | 1/2000 | Abele et al. | |
| 6,012,451 A | 1/2000 | Palmer | |
| 6,048,332 A | 4/2000 | Duffy et al. | |
| 6,058,933 A | 5/2000 | Good et al. | |
| 6,110,192 A | 8/2000 | Ravenscroft et al. | |
| 6,129,547 A | 10/2000 | Cise | |
| 6,169,123 B1 | 1/2001 | Cercone | |
| 6,210,364 B1 | 4/2001 | Anderson | |
| 6,214,895 B1 | 4/2001 | Cercone | |
| 6,227,200 B1 | 5/2001 | Crump et al. | |
| 6,240,321 B1 | 5/2001 | Janke et al. | |
| 6,248,088 B1 | 6/2001 | Yoon | |
| 6,264,631 B1 | 7/2001 | Willis et al. | |
| 6,264,633 B1 | 7/2001 | Knorig | |
| 6,277,089 B1 | 8/2001 | Yoon | |
| 6,290,447 B1 | 9/2001 | Siemonsen et al. | |
| 6,312,421 B1 | 11/2001 | Boock | |
| 6,322,586 B1 | 11/2001 | Monroe et al. | |
| 6,364,856 B1 | 4/2002 | Ding et al. | |
| 6,394,093 B1 | 5/2002 | Lethi | |
| 6,395,012 B1 | 5/2002 | Yoon et al. | |
| 6,398,266 B1 | 6/2002 | Crump | |
| 6,409,716 B1 | 6/2002 | Sahatjian et al. | |
| 6,494,203 B1 | 12/2002 | Palmer | |
| 6,524,274 B1 | 2/2003 | Rosenthal et al. | |
| 6,526,977 B1 | 3/2003 | Göbel | |
| 6,543,451 B1 | 4/2003 | Crump et al. | |
| 6,551,272 B2 | 4/2003 | Göbel | |
| 6,572,813 B1 | 6/2003 | Zhang et al. | |
| 6,584,970 B1 | 7/2003 | Crump et al. | |
| 6,588,425 B2 | 7/2003 | Rouns et al. | |
| 6,588,427 B1 | 7/2003 | Carlsen et al. | |
| 6,591,123 B2 | 7/2003 | Fein et al. | |
| 6,602,218 B2 | 8/2003 | Yoon | |
| 6,602,219 B2 | 8/2003 | Madsen et al. | |
| 6,606,510 B2 | 8/2003 | Swedlow et al. | |
| 6,609,520 B1 | 8/2003 | Carlsen et al. | |
| 6,612,304 B1 | 9/2003 | Cise et al. | |
| 6,613,025 B1 | 9/2003 | Palasis | |
| 6,615,835 B1 | 9/2003 | Cise et al. | |
| 6,620,128 B1 | 9/2003 | Simhambhatla | |
| 6,622,864 B1 * | 9/2003 | Debbs et al. | 206/438 |
| 6,623,450 B1 | 9/2003 | Dutta | |
| 6,629,530 B2 | 10/2003 | Cise | |
| 6,632,091 B1 | 10/2003 | Cise et al. | |
| 6,651,664 B1 | 11/2003 | Lomholt | |

(56) References Cited

U.S. PATENT DOCUMENTS

| | | | |
|---|---|---|---|
| 6,662,941 B2 * | 12/2003 | Lowry et al. | 206/204 |
| 6,688,306 B1 | 2/2004 | Cise et al. | |
| 6,698,424 B2 | 3/2004 | Madsen et al. | |
| 6,726,696 B1 | 4/2004 | Houser et al. | |
| 6,732,734 B2 * | 5/2004 | Ogushi et al. | 128/207.15 |
| 6,745,773 B1 | 6/2004 | Gobel | |
| 6,767,340 B2 | 7/2004 | Willis et al. | |
| 6,769,430 B1 | 8/2004 | Carlsen et al. | |
| 6,770,066 B1 | 8/2004 | Weaver et al. | |
| 6,786,876 B2 | 9/2004 | Cox | |
| 6,790,221 B2 | 9/2004 | Monroe et al. | |
| 6,802,317 B2 | 10/2004 | Göbel | |
| 6,805,125 B1 | 10/2004 | Crump et al. | |
| 6,808,521 B1 | 10/2004 | McMichael | |
| 6,908,449 B2 | 6/2005 | Willis et al. | |
| 6,916,307 B2 | 7/2005 | Willis et al. | |
| 6,923,786 B2 | 8/2005 | Rouns et al. | |
| 7,040,321 B2 | 5/2006 | Göbel | |
| 7,084,884 B1 | 8/2006 | Nelson et al. | |
| 7,085,597 B2 | 8/2006 | Fein et al. | |
| 7,234,597 B2 * | 6/2007 | Rowe et al. | 206/438 |
| 7,261,105 B2 | 8/2007 | Fukunaga et al. | |
| 2001/0041861 A1 | 11/2001 | Gobel | |
| 2002/0032407 A1 | 3/2002 | Willis et al. | |
| 2002/0077603 A1 | 6/2002 | Willis et al. | |
| 2002/0077604 A1 | 6/2002 | Willis et al. | |
| 2002/0078960 A1 | 6/2002 | Cise | |
| 2002/0078963 A1 | 6/2002 | Rouns et al. | |
| 2002/0082552 A1 | 6/2002 | Ding et al. | |
| 2002/0091375 A1 | 7/2002 | Sahatjian et al. | |
| 2002/0193753 A1 | 12/2002 | Rouns et al. | |
| 2003/0000526 A1 | 1/2003 | Gobel | |
| 2003/0066532 A1 | 4/2003 | Gobel | |
| 2003/0069620 A1 | 4/2003 | Li | |
| 2003/0111077 A1 | 6/2003 | Hooser et al. | |
| 2003/0116162 A1 | 6/2003 | Madsen et al. | |
| 2003/0116963 A1 | 6/2003 | Teuscher et al. | |
| 2003/0225369 A1 | 12/2003 | McMichael et al. | |
| 2003/0225392 A1 | 12/2003 | McMichael et al. | |
| 2003/0225393 A1 | 12/2003 | McMichael et al. | |
| 2004/0006261 A1 | 1/2004 | Swedlow et al. | |
| 2004/0024363 A1 | 2/2004 | Goldberg | |
| 2004/0079376 A1 | 4/2004 | Melker | |
| 2004/0092870 A1 | 5/2004 | Squire et al. | |
| 2004/0106899 A1 | 6/2004 | McMichael et al. | |
| 2004/0106900 A1 | 6/2004 | Triebes et al. | |
| 2004/0106901 A1 | 6/2004 | Letson et al. | |
| 2004/0193100 A1 | 9/2004 | Van Hooser et al. | |
| 2004/0193101 A1 | 9/2004 | Van Hooser et al. | |
| 2004/0195131 A1 * | 10/2004 | Spolidoro | 206/438 |
| 2004/0195132 A1 * | 10/2004 | Sheetz et al. | 206/438 |
| 2004/0211682 A1 * | 10/2004 | Brander | 206/204 |
| 2004/0215142 A1 | 10/2004 | Matheis et al. | |
| 2004/0255952 A1 | 12/2004 | Carlsen et al. | |
| 2005/0004560 A1 | 1/2005 | Cox | |
| 2005/0033267 A1 | 2/2005 | Decaria | |
| 2005/0033268 A1 | 2/2005 | Decaria | |
| 2005/0033269 A1 | 2/2005 | Decaria | |
| 2005/0038381 A1 | 2/2005 | McMichael | |
| 2005/0040061 A1 * | 2/2005 | Opie et al. | 206/363 |
| 2005/0065468 A1 | 3/2005 | Goebel | |
| 2005/0124932 A1 | 6/2005 | Foster et al. | |
| 2005/0124935 A1 | 6/2005 | McMichael | |
| 2006/0025660 A1 | 2/2006 | Swedlow et al. | |
| 2006/0030765 A1 | 2/2006 | Swedlow et al. | |
| 2006/0135951 A1 | 6/2006 | Meek et al. | |
| 2006/0217604 A1 | 9/2006 | Fein et al. | |
| 2006/0217605 A1 | 9/2006 | Fein et al. | |
| 2006/0217606 A1 | 9/2006 | Fein et al. | |
| 2006/0217607 A1 | 9/2006 | Fein et al. | |
| 2006/0217608 A1 | 9/2006 | Fein et al. | |
| 2006/0229510 A1 | 10/2006 | Fein et al. | |
| 2006/0229511 A1 | 10/2006 | Fein et al. | |

FOREIGN PATENT DOCUMENTS

| | | |
|---|---|---|
| EP | 1005877 A2 | 6/2000 |
| EP | 1135184 | 6/2000 |
| EP | 1267981 B1 | 1/2003 |
| WO | WO 00/32262 A1 | 6/2000 |
| WO | WO 03/045487 A2 | 6/2003 |
| WO | WO 2004/101046 A1 | 11/2004 |

OTHER PUBLICATIONS

Sheridan PED-Soft Uncuffed Endotracheal Tubes, Teleflex Medical—Hudson RCI, Apr. 2010, pp. 1-3.

Sheridan Performed Endotracheal Tubes, Teleflex Medical—Hudson RCI, Apr. 2010, pp. 1-3.

Sheridan Sher-I-Bronch Endobrochial Tubes, Teleflex Medical—Hudson RCI, Apr. 2010, pp. 1-4.

Sheridan ETCO2 Uncuffed Endotracheal Tubes, Monitoring Lumen Tubes, Hudson RCI, 2010, pp. 1-2.

Rusch, Easytube Double Lumen, Teleflex Medical, http://www.teleflexmedical.com/prod_rusch.php, 2009, pp. 1-7.

Teleflex ISIS HVT, Cuffed Endotracheal Tubes, Hudson RCI-Products, 2010, pp. 1-5.

Sheridan NAZ-AL, Teleflex Medical—Hudson RCI, Apr. 2010, pp. 1-2.

Sheridan CF, Teleflex Medical—Hudson RCI, Apr. 2010, pp. 1-2.

Sheridan EZ-ENDO, Teleflex Medical—Hudson RCI, Apr. 2010, pp. 1-2.

Sheridan LTS, Teleflex Medical—Hudson RCI, Apr. 2010, pp. 1-2.

Sheridan Uncuffed, Teleflex Medical—Hudson RCI, Apr. 2010, pp. 1-2.

Sheridan Flex-C-PAP, Teleflex Medical—Hudson RCI, Apr. 2010, pp. 1-2.

Sheridan Laser-Trach, Teleflex Medical—Hudson RCI, Apr. 2010, pp. 1-2.

* cited by examiner

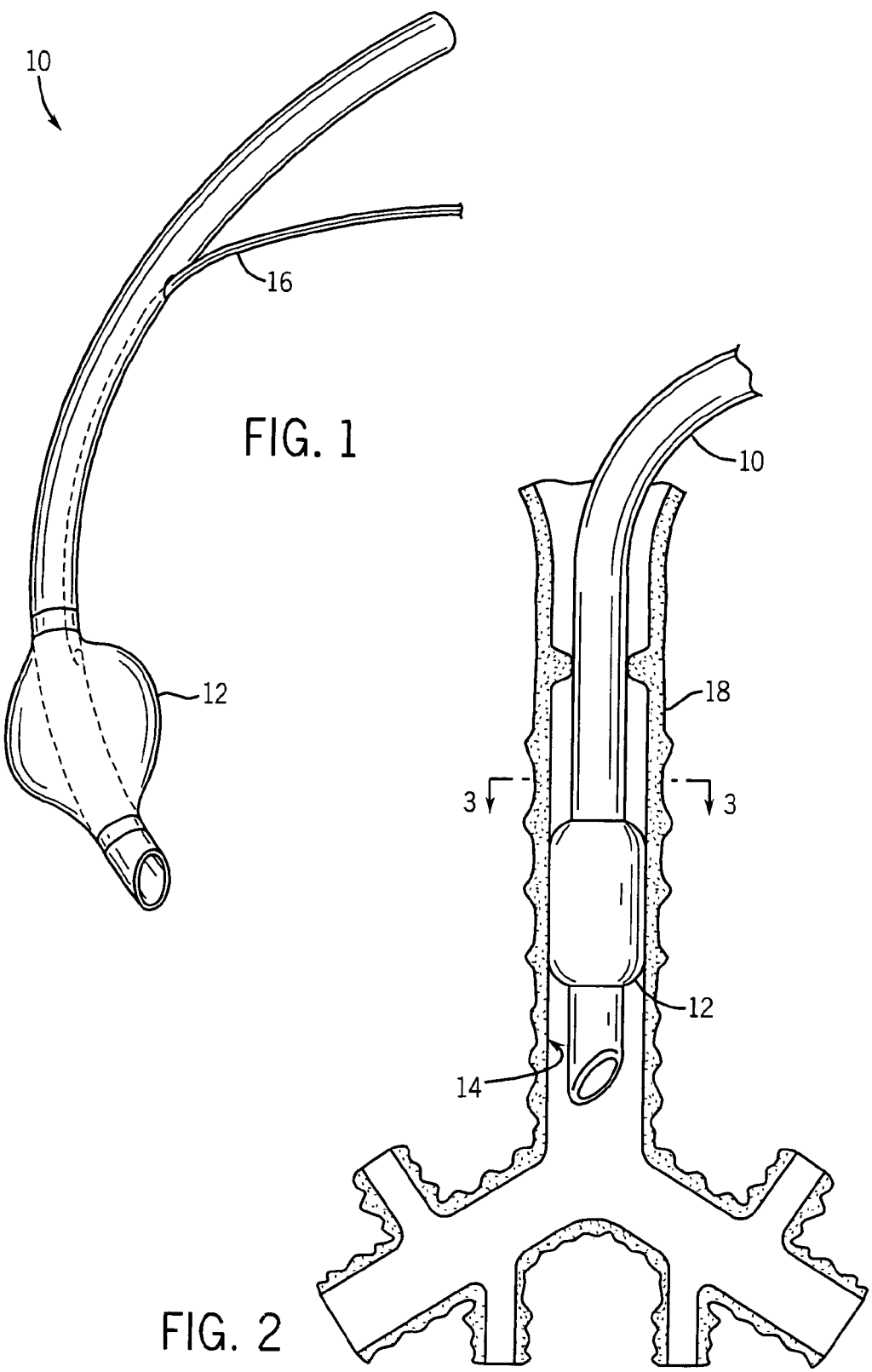

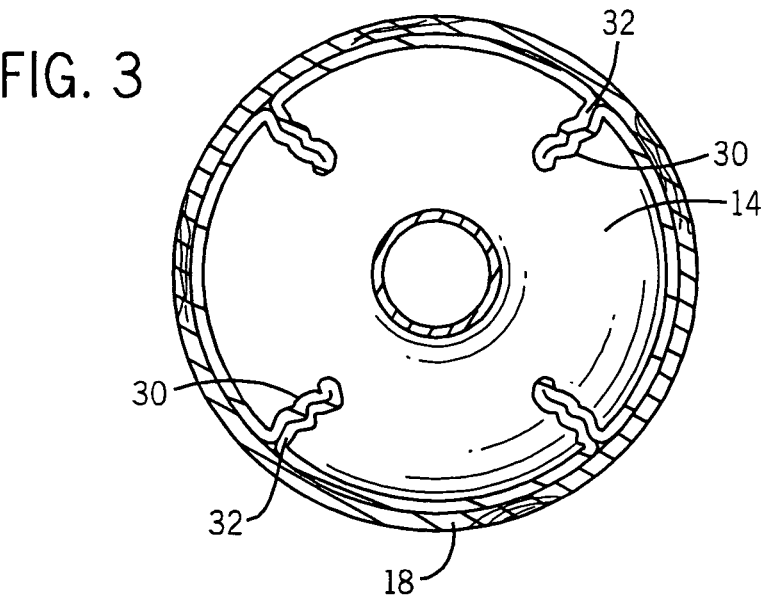
FIG. 3
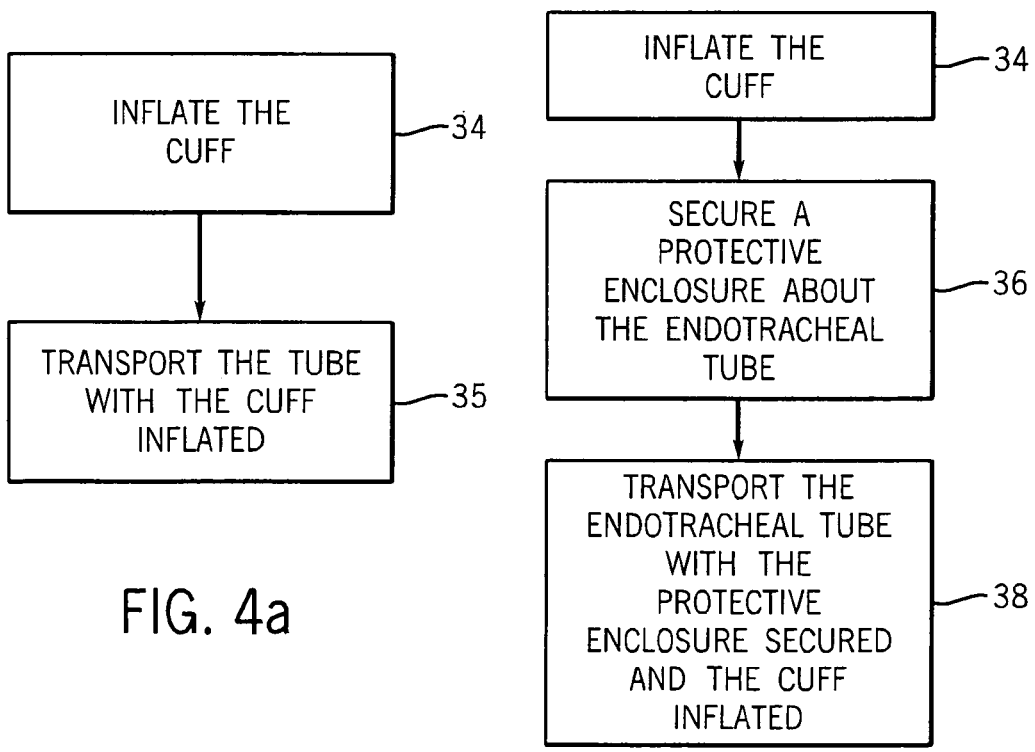
FIG. 4a
FIG. 4b

METHOD FOR SHIPPING AND PROTECTING AN ENDOTRACHEAL TUBE WITH AN INFLATED CUFF

BACKGROUND OF THE INVENTION

1. Field of the Invention

The present invention relates to medical devices, and more particularly, to airway products, such as tracheal tubes and cuffs.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the course of treating a patient, a tube or other medical device may be used to control the flow of air, food, fluids, or other substances into the patient. For example, medical devices such as tracheal tubes may be used to control the flow of one or more substances into or out of a patient. In many instances it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

For example, tracheal tubes may be used to control the flow of air or other gases through a patient's trachea. Such tracheal tubes may include endotracheal (ET) tubes or tracheostomy tubes. To seal these types of tracheal tubes, an inflatable cuff may be associated with these tubes. When inflated, the cuff generally expands into the surrounding trachea to seal the tracheal passage around the tube.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided a package for a medical device with an inflatable region, comprising a substantially non-stretchable region that substantially conforms to the shape of the inflatable region of the medical device when the inflatable region is inflated.

There is also provided a shipping assembly, comprising; a medical device having an inflated region; and a package, comprising; a substantially non-stretchable region that substantially conforms to the shape of the inflated region of the medical device.

There is also provided a method of transporting, comprising transporting an inflated medical device in a package.

There is also provided a method of packaging a medical device, comprising; inflating an inflatable region of a medical device; and securing a protective package about the inflated inflatable region, wherein the protective package substantially conforms to the inflated inflatable region.

BRIEF DESCRIPTION OF THE DRAWINGS

Advantages of the invention may become apparent upon reading the following detailed description and upon reference to the drawings in which:

FIG. 1 illustrates an endotracheal tube with an inflatable cuff in accordance with aspects of the present technique;

FIG. 2 illustrates the inflatable cuff of the present techniques inserted into a patient's trachea;

FIG. 3 is a cross-sectional view of the wrinkled region of the inflated cuff of FIG. 2 taken along line 3-3 of FIG. 2;

FIG. 4a is a flowchart depicting a method for transporting a cuff while inflated;

FIG. 4b is a flowchart depicting a method for transporting a tube and cuff while the cuff is inflated within a protective enclosure;

DETAILED DESCRIPTION OF SPECIFIC EMBODIMENTS

Figure 5:
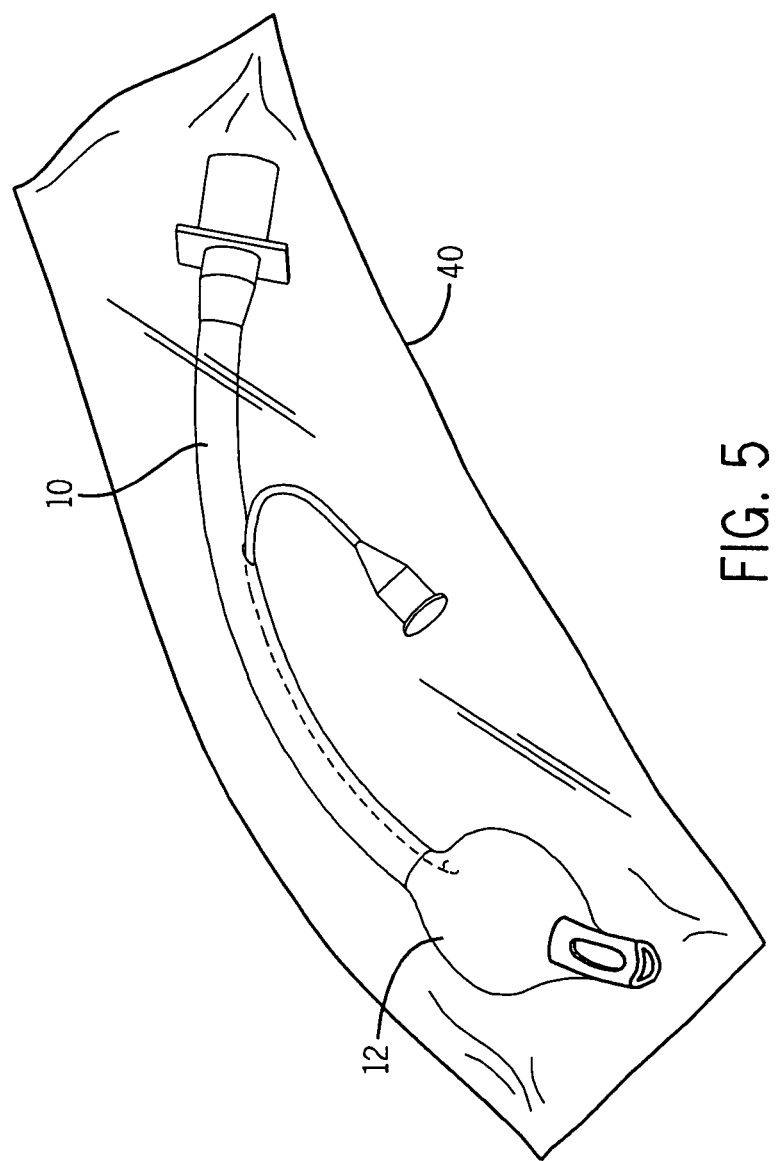
FIG. 5 illustrates an endotracheal tube with an inflated cuff in a single package for transportation.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

With tracheal tubes, folds and wrinkles in the cuff may decrease the cuff's ability to seal against the walls of the tracheal passage. For example, tracheal tubes are generally shipped with the cuff portion deflated. When the cuff is deflated by exposure to atmospheric pressure or a vacuum, the material of the cuff region folds on itself due to the lack of internal pressure. While shipped or stored in this state for an extended period, the cuff may develop permanent folds and wrinkles in the cuff material or become predisposed to form folds or wrinkles in particular portions of the cuff material. Therefore, such a cuff may contain wrinkles and folds when inflated in the trachea. These folds may serve as leak paths that allow air and liquids to flow past the cuff and enter the lung.

Additionally sterilization of a tracheal tube prior to use may promote additional wrinkles and folds during use. During sterilization, the tracheal tube and the cuff may be exposed to elevated temperatures and decreased external pressure. When an inflated cuff is sterilized, the elevated temperatures and the decreased pressure may cause the cuff to deform in size and shape. Therefore, once inserted and inflated in the trachea, such a cuff may not be the desired shape or size and/or may form undesired folds and wrinkles. Additionally, while the cuff is in the deflated state, increased temperatures may promote the setting of wrinkles that are predisposed about the deflated cuff. As noted above, these folds may serve as leak paths that allow air and liquids to flow past the cuff and enter into the lung.

Thus, it would be desirable to provide a medical tube having a sealing member, such as a cuff or other suitable device, which may substantially seal the passage in which the sealing member is inserted so that air, oxygen, or medications may be introduced into the lungs. In accordance with some aspects of the present technique, a cuff of an endotracheal tube is inflated prior to transporting to prevent the onset of permanent wrinkles and folds in the cuff. Further, in accordance with some aspects of the present technique, a protective packaging is provided to prevent deformation of the cuff and to protect the cuff while the cuff is inflated.

A variety of medical devices are designed to be inserted within cavities or passages of the human body. Examples of such medical devices include catheters, stents, feeding tubes, intravenous tubes, breathing tubes, and so forth. In many instances it is desirable that a seal be formed between the medical device and the surrounding passage or cavity. An example of such a medical device is an endotracheal tube 10, as depicted in FIG. 1. The endotracheal tube 10 includes an inflatable cuff 12 that may be inflated at low pressure (approximately 25 cm $H_2O$ or less) to form a seal against the trachea wall 14 (see FIG. 2). Typically the cuff 12 is inflated and deflated via a tube 16 in communication with the cuff 12. It is also noted that other medical devices may require inflation at high pressures than those required of an endotracheal tube 10.

For simplicity, the present example describes the use of the cuff 12 in the context of an endotracheal tube. However, those of ordinary skill in the art will appreciate that the cuff 12 can be used with other medical devices, such as those listed above, or with devices where it is generally desirable to form a seal between the device and a surrounding passage or pathway. Therefore, it should be understood that the present examples and descriptions are merely exemplary and are not intended to limit the scope of the present technique.

When inflated, the cuff 12 may assume a cylindrical or barrel shape that may include a short tapered section designed to connect the ends of the cuff 12 to a narrower object, such as the endotracheal tube 10. When inflated, the diameter of the cuff 12 is typically larger than the size of the trachea 18. Therefore, when the deflated cuff 12 is inserted into a patient's trachea 18 and inflated to the recommended cuff pressures, the cuff 12 may be unable to inflate to its maximum diameter and may fold in on itself. The folding may cause wrinkles 30 and leak paths 32 to form (see FIG. 3). In addition to the wrinkles 30 caused by the inflation of the cuff 12, wrinkles may already be present in the cuff 12, or predisposed to form at certain points on the cuff 12, prior to inflation. For example, if the cuff 12 had been stored in a deflated state, the material of the cuff 12 may be predisposed to crease and wrinkle as discussed above. Such creases and wrinkles in the deflated state may lead to this predisposition due to the 'memory' of the material of the cuff 12.

Returning now to FIG. 1, in accordance with the present technique, the endotracheal tube 10 is depicted with the cuff 12 inflated. When the cuff 12 is inflated without a constraint about its diameter, the cuff 12 may contain few or no wrinkles about it diameter. Due to the lack of wrinkles present in the inflated cuff 12, transporting the endotracheal tube 10 with the cuff 12 in an inflated state may prevent the material from forming a memory of wrinkles in the material of the cuff 12. As an additional advantage, transporting the cuff 12 in an inflated state allows the end user to make an instant assessment of the state of the cuff 12. For example, a medical practitioner may be able to determine quickly the ability of the cuff 12 to hold pressure by observing the inflated state of the cuff 12. This may reduce the amount of preparation required, as the medical practitioner may otherwise have to inflate the cuff 12 and examine it for leaks prior to use. In one embodiment, as depicted in FIG. 4a, a method for transporting the endotracheal tube 10 may include at least partially inflating (Block 34) the cuff 12 prior to transporting (Block 35) the endotracheal tube 10. For example, the cuff 12 may be shipped with an internal pressure of 20 to 75 cm $H_2O$. In yet another embodiment depicted in FIG. 4b, the method of transporting the endotracheal tube 10 may include transporting (Block 38) the endotracheal tube 10 and inflated cuff 12 inside of a protective enclosure 44 (see FIG. 6) that has been secured (Block 36) to the endotracheal tube 10. For example, as depicted in FIG. 5, the endotracheal tube 10 may be enclosed in a protective enclosure 40 during transporting. As one of ordinary skill in the art will appreciate, the protective enclosure 40 may take a variety of forms and shapes to provide the desired protective function (e.g., protection from penetration by air or liquid).

Although transporting the endotracheal tube 10 with the cuff 12 inflated may reduce the likelihood of wrinkles forming in the cuff 12, it may not fully protect the cuff 12 from wrinkles and deformation that may occur during sterilization and transporting. For instance, after an endotracheal tube has been manufactured and packaged, it may undergo a sterilization process. This process may include an evacuation step to remove air from the sterilization chamber in order to expose the tube 10 to ethylene oxide (a gas used commonly for sterilization). If the inflated cuff 12 is exposed to this environment without support, the difference in internal and external pressure may cause the cuff 12 to deform in shape and/or expand in diameter. If deformation occurs, and as the diameter of the of the cuff 12 increases relative to the patients trachea 18 during use, there is an increased potential that the cuff 12 will not seal properly and may fold over itself. Thus, such deformation during sterilization may lead to an increased number of wrinkles 30 and leak paths 32 when the cuff 12 is in use.

Further, during storage and transportation with the cuff 12 inflated, the cuff 12 may be exposed to external contact and forces that may cause the formation of wrinkles or deformation on the cuff 12. For example, if the endotracheal tube was placed on a surface or packaged against other devices for an extended period of time, the portion of the inflated cuff 12 that experiences the external force may deform and/or become wrinkled. In addition to these concerns, if the cuff 12 is inflated during storage and transport, it has an increased potential to be punctured. Therefore, it is desirable that the cuff 12 be supported and protected during sterilization, storage, and transport.

Figure 6:
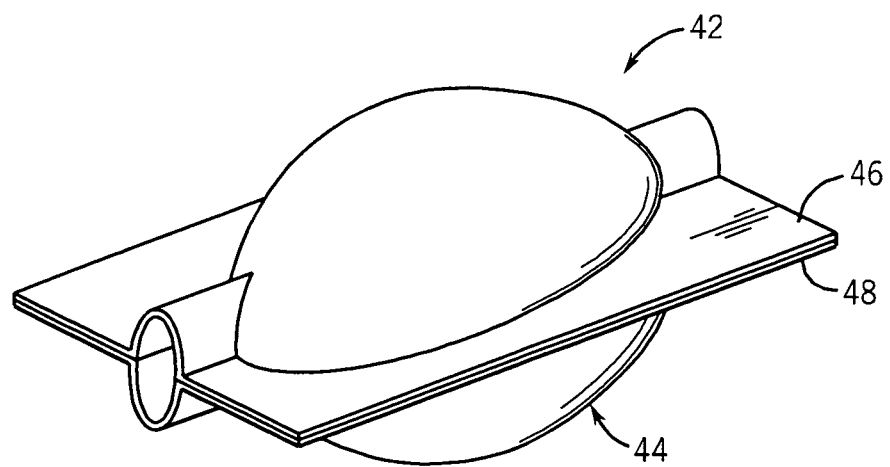
FIG. 6 illustrates a perspective view of a package to enclose the inflatable cuff.

Turning to FIG. 6, in accordance with the present technique, a package 42 for the endotracheal tube 10 with the inflated cuff 12 is depicted. In one embodiment, the package 42 includes a substantially non-stretchable region 44 that substantially conforms to the shape of the cuff 12 when the cuff 12 is inflated. It is desirable for the package 42 to include a non-stretchable region 44 about the cuff 12 to prevent the cuff 12 from expanding when exposed to increased temperatures and decreased pressures. In these instances, the non-stretchable region 44 may not conform to the deflated shape of the cuff 12, but merely conform to the desired inflated shape of the cuff 12. In the embodiment depicted in FIG. 6, the non-stretchable region 44 generally conforms to the shape of the inflated cuff 12, so it may be spherical or barrel-like in shape, for example. As one of ordinary skill in the art will appreciate, the shape of the non-stretchable region 44 may vary to accommodate the shape of the inflated cuff 12. Further, as depicted in FIG. 6, the package 42 includes a top 46 and a bottom 48 which maybe affixed about the inflated cuff 12 and possibly about at least a portion of the endotracheal tube 10. Although this exemplary embodiment describes the package 42 as generally conforming to the shape and size of the inflated cuff 12, the package 42 may take any shape or form that provides sufficient support and/or protection of the inflated cuff 12.

The package 42 may be formed from various materials that are non-stretchable and capable of substantially conforming to the shape of the cuff 12. For example, in one embodiment, the package, 42 may be formed from polystyrene. As one ordinarily skilled in the art will appreciate, the package may be formed from various similar materials capable of meeting the criteria of packaging listed above. For example, other materials may include, but are not limited to, polycarbonate, polypropylene, polyethylene terephthalate (PET), recycled polyethylene terephthalate (RPET), amorphous polyethylene terephthalate, high density polyethylene (HDPE), low density polyethylene (LDPE), polyphenylene sulfide (RPS), polyvinyl chloride (PVC), or polyvinylidene chloride (PVDC), polyethylene terephthalate glycol (PETG).

Figure 7:
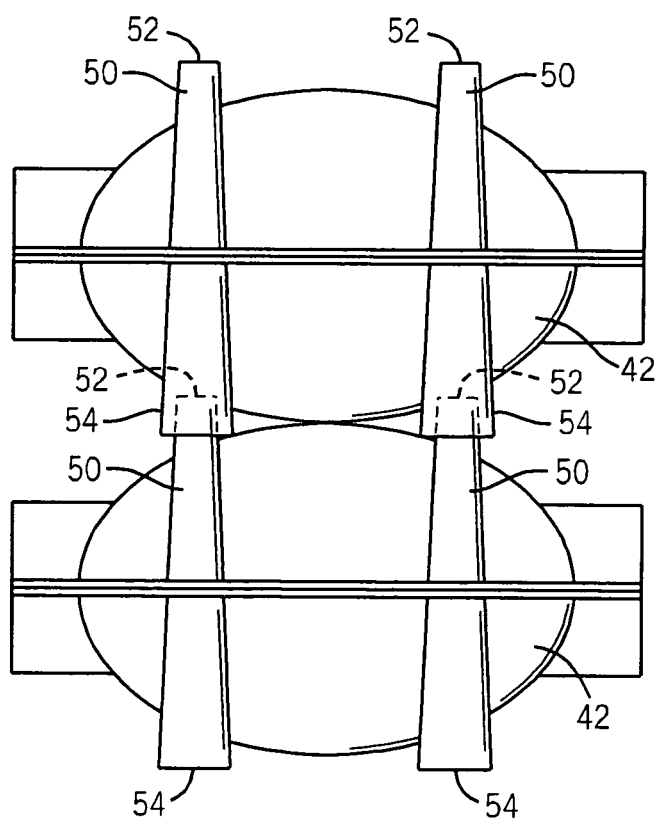
FIG. 7 illustrates a side view of an alternate configuration of the package having feet features, wherein two packages are stacked one on top of the other.

In various exemplary embodiments of the package 42, additional features may be included. For example, in one embodiment depicted in FIG. 7, the package 42 may include feet 50 that provide for a place to rest the package 42. As one of ordinary skill in the art will appreciate, the feet 50 may take various forms and shapes. For example, as depicted in FIG. 7, the feet 50 may include a tapered end 52 and a flared end 54, wherein the flared end 54 is capable of accepting the tapered end 52 to allow multiple packages 42 to be stacked or secured to one another when the packages 42 are closed. Further, in this embodiment, the feet 50 may provide a stable support for the upper and lower halves of the package 42 after it has been opened. This may be particularly useful for a clinician, since the endotracheal tube 10 may be laid with the inflated cuff 12 in one half of the opened package while the clinician is preparing to insert the tube 10 into a patient. By temporarily storing the tube 10 in this manner, it remains stable and sterile.

Figure 8:
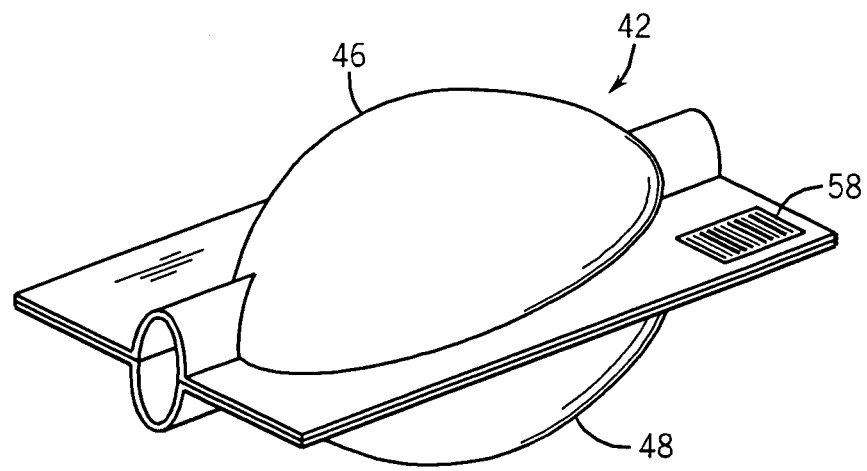
FIG. 8 illustrates a perspective view of an alternate configuration of the package having a barcode identification feature.

To identify the contents of the package 42, the package 42 may include an identifying feature. For example, as depicted in FIG. 8, the identifying feature may include a barcode 58. The barcode 58 may be scanned and interpreted to identify the package contents or other relevant information. In another embodiment, the identifying feature may include the color of a portion of the package 42 or of the entire package 42. For example, top 46 or the bottom 48 of the package 42 may be formed from material of a given color to indicate the contents of the package 42. As one of ordinary skill in the art will appreciate, the use of a color as an identifying feature may take various forms. For instance, the color may be incorporated into the package 42 material, or it may be subsequently added to the package 42 (e.g., a sticker or label).

Figure 9:
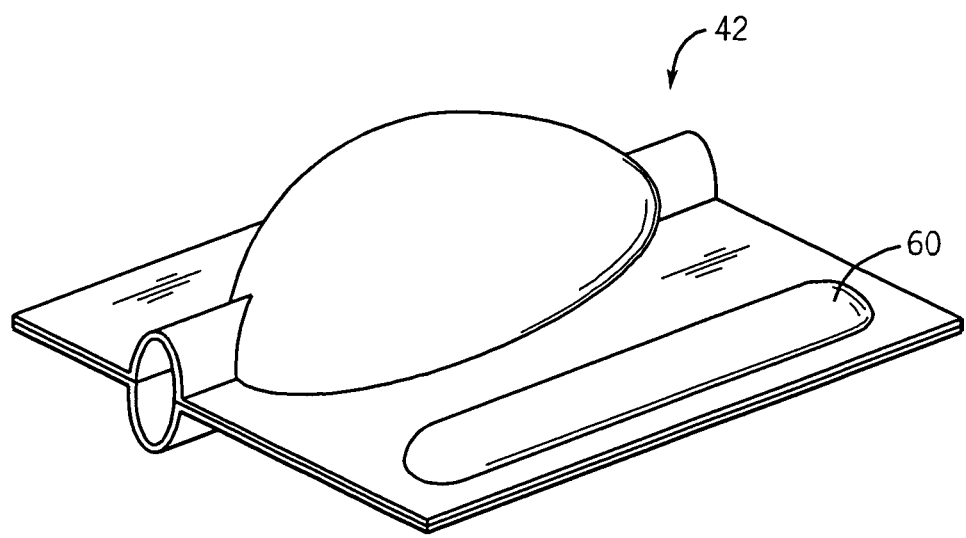
FIG. 9 illustrates a perspective view of an alternate configuration of the package having a storage feature.

A storage feature 60 may be included in the package 42 as depicted in FIG. 9. In one embodiment, the storage feature 60 may provide for storage of substances that may be used by a clinician to insert the tube 10 into a patient, including, but not limited to lubricants and other liquids. In another embodiment, the storage feature 60 may provide for storage of a syringe or other medical device that may be used by a clinician to insert or adjust the tube 10. The storage feature may also provide for storage of a $CO_2$ detector, or other device that may be used to confirm the proper placement of the endotracheal tube. As one of ordinary skill in the art will appreciate, the storage feature 60 may take various forms and may provide storage for any number of devices and substances. For example, the storage feature 60 may be incorporated into a package 42 with feet 50 as described previously. With the feet 60 providing stability of the package 42, the package may be laid open by the clinician during use of the tracheal tube 10 or other medical procedure. Once open, the storage feature 60 may provide additional trays for placement of substances (e.g. lubricants) or medical devices which may be accessed easily during medical procedures.

Figure 10:
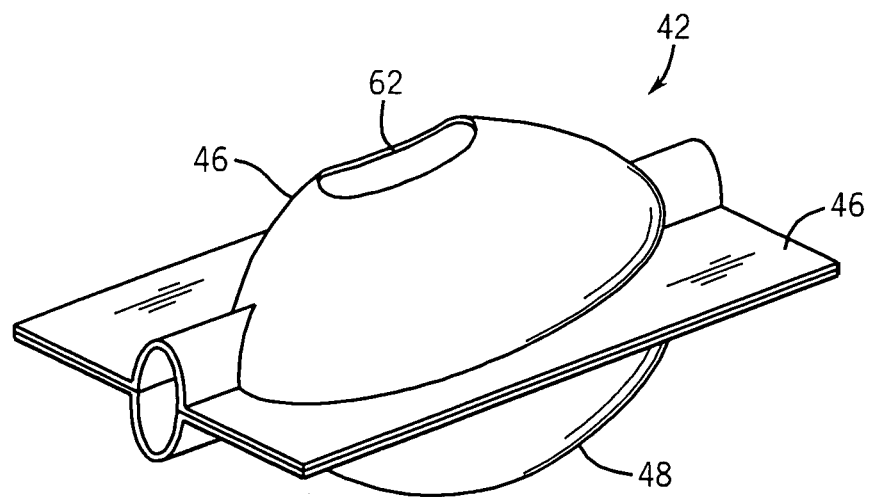
FIG. 10 illustrates a perspective view of an alternate configuration of the package having an aperture.

To provide for inspection of the contents of the package 42, an aperture 62 may be included in the package 42. For example, as depicted in FIG. 10, an aperture may be located on the top 46 of the package 42. Such an aperture 62 may allow inspection of the contents of the package 42 while maintaining radial support for the contents. For example, the aperture 62 may be large enough for a user to insert their finger for physical examination of the contents, but the aperture 62 may be small enough relative to the size of the package 42 to support the majority of the contents (e.g. the cuff 12). As one of ordinary skill in the art will appreciate, the aperture 62 may be varied in size and location to accommodate various applications.

The package 42 may be formed of transparent or semi-transparent material, in another embodiment, to provide for visual inspection of the contents of the package 42. For instance, the use of a transparent material for the package 42 may allow the user to visually inspect the inflated state and size of the cuff 12.

The package 42 may be formed from a pliable material (e.g., Low Density Polyethylene) in an embodiment that provides for physical examination of the contents of the package 42 when a portion of the package 42 is depressed. For instance, a user may be able to squeeze the package 42 to determine if the inflated cuff 12 of the endotracheal tube 10 is inflated or deflated. It is typically desirable that materials be used that are pliable and capable of providing sufficient support while not being susceptible to stretching. It should be noted, however, that such a pliable material may not fully support and protect the cuff 12. For example, a pliable material may be unable to support the cuff 12 from being depressed or punctured during transportation of a multitude of devices stacked one upon another. In light of this concern, a pliable material that is capable of providing sufficient support for the cuff may be advantageous.

Figure 11:
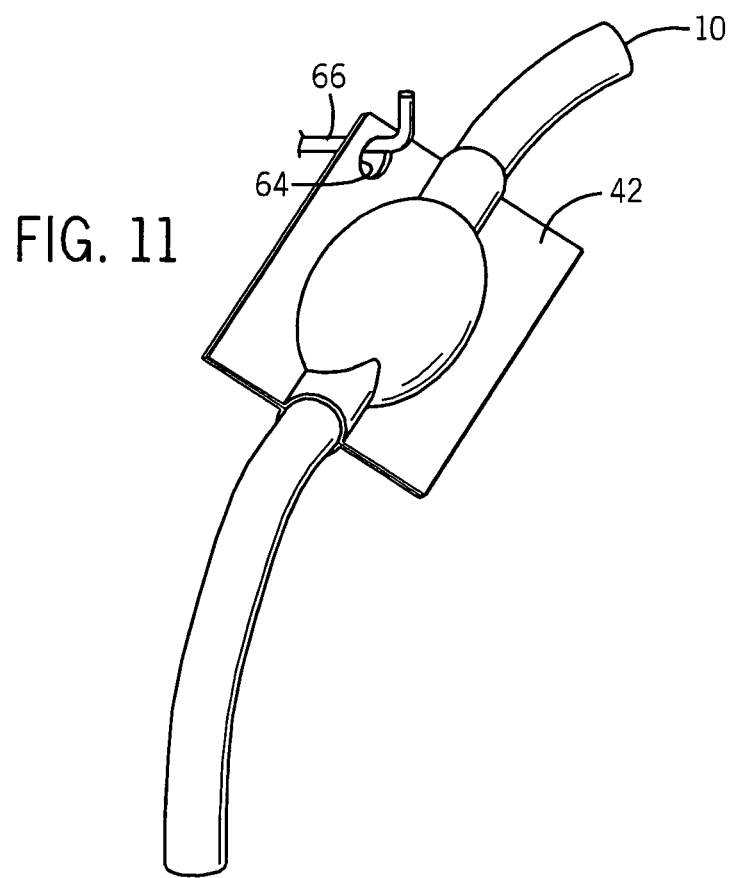
FIG. 11 illustrates a perspective view of an alternate configuration of the package having a hanging feature.

The package 42 may include a hanging feature 64 to facilitate hanging of the package 42 and the endotracheal tube 10. Providing for hanging of the package 42 may prove useful in situations where space is limited and where access and organization is desirable. An example may include a surgery room where the clinician may need devices (e.g., endotracheal tube 10) available for immediate use. As depicted in FIG. 11, an embodiment of the hanging feature 64 may include a hole that allows for the package 42 and the endotracheal tube 10 to be hung on a hook 66. As one of ordinary skill in the art will appreciate, the hanging feature 64 may take various forms. For example, the hanging feature 64 may take the form of a hook, loop, or eye that are capable of hanging on other hooks, loops, eyes, racks, or other convenient locations (e.g., bedrails and surgical tables).

Figure 12:
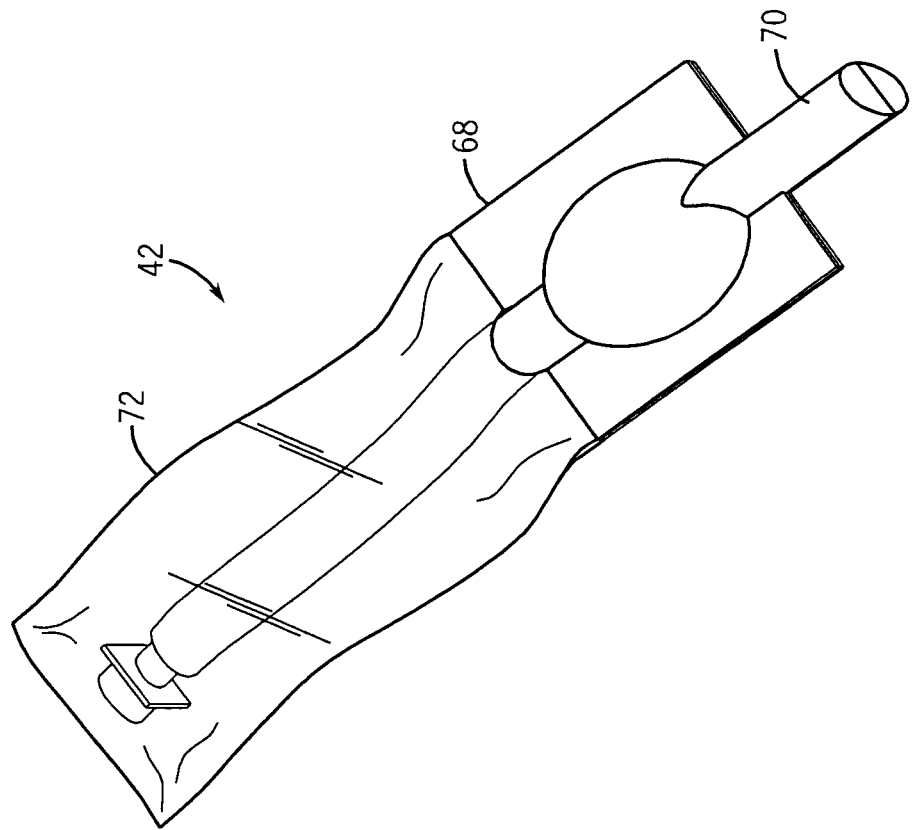
FIG. 12 illustrates a perspective view of an alternate configuration of the package wherein the package encloses the entire tracheal tube.

The package 42 may include a portion to enclose the cuff 12 and the remainder of the tracheal tube 10. For example, as depicted in FIG. 12, the package 42 may include of a non-stretchable region 68, a tip enclosure 70 and tube enclosure 72. As depicted in FIG. 12, the non-stretchable region 68 may be joined to the tip enclosure 70 and the tube enclosure 72 to provide a single package 42 that encloses the tracheal tube 10, including the cuff 12. As one of ordinary skill in the art will appreciate, the form and shape of the package 42 may vary to enclose the tracheal tube 10 and cuff 12 in a single package 42. For instance, the non-stretchable region 68 may encompass all or a significant amount of the endotracheal tube 10 and the cuff 12.

Figure 13:
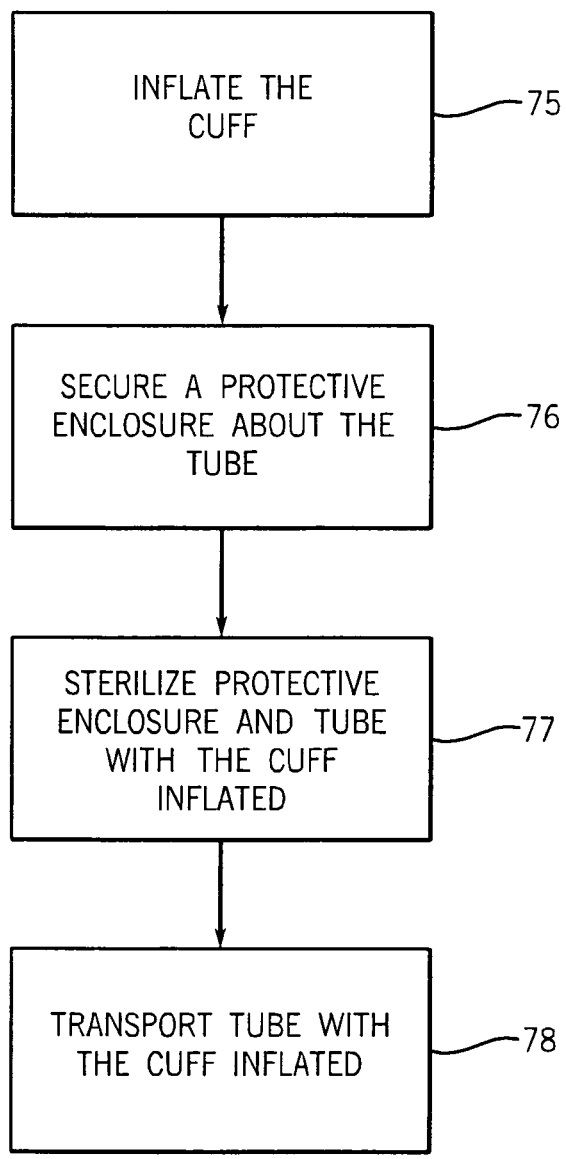
FIG. 13 is a flowchart depicting a method of packaging an endotracheal tube with the cuff inflated.

FIG. 13 illustrates an exemplary method of packaging the tracheal tube 10 and the cuff 12. In one implementation, the cuff 12 is inflated (Block 75). For example, the cuff 12 may be inflated to a pressure of 20 to 75 cm $H_2O$. After inflating the cuff 12, the package 42 is secured about the inflated cuff 12 (Block 76). In the depicted embodiment, the package 42 and the inflated cuff 12 are then sterilized (Block 77) together before being transported for use (Block 78). As an example, sterilization may be accomplished by exposing the package 42, the tracheal tube 10, and the inflated cuff 12 to temperatures of approximately 60 C and/or to a vacuum. As one of ordinary skill in the art will appreciate, these steps of packaging may take place in a variety of orders. For example, the package 42 may be secured about the tracheal tube 10 prior to the inflation of the cuff 12. In another embodiment, the sterilization of the tracheal tube 10, the cuff 12 and the package 42 may take place before securing the package 42 about the cuff 12.

Figure 14:
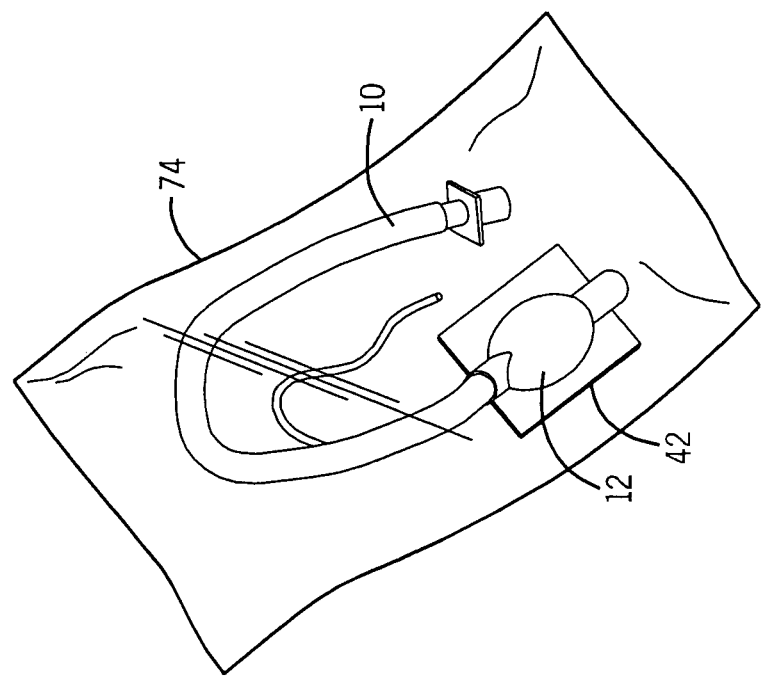
FIG. 14 illustrates a perspective view of an alternate configuration of the packaging wherein a package wrap encloses the tracheal tube and the package about the inflatable cuff.

In another embodiment of the method illustrated in FIG. 13, securing the package 42 about the cuff 12 (Block 76), includes enclosing the entire tracheal tube 10 in a single package 42 (see FIG. 12). This embodiment provides for a single package that encloses the tracheal tube 10 and the cuff 12. In another embodiment, in addition to securing the package 42 about the cuff 12, a package wrap 74 is provided about the endotracheal tube 10, the cuff 12, and the package 42 (see FIG. 14). This embodiment provides two separate packages: the package 42 enclosing the cuff 12, and the package wrap 74 enclosing the endotracheal tube 10, the cuff 12, and the package 42.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A package for a medical device with an inflatable region, comprising:
an inflatable region coupled to a tracheal tube;
a protective enclosure comprising a substantially non-stretchable region that substantially conforms to the shape of the inflatable region of the medical device when the inflatable region is inflated to an inflated configuration comprising an internal cuff pressure sufficient to remove wrinkles from the cuff when inflated outside the patient without a constraint against a diameter of the cuff, wherein the inflatable region is disposed within the protective enclosure, and wherein the inflatable region is inflated within the protective enclosure to an internal pressure between 20 to 75 cm $H_2O$.

2. The package of claim 1, comprising feet configured to provide a support for the package.

3. The package of claim 2, wherein the feet comprise features configured to interface with features of similar packages to provide for stacking of multiple packages.

4. The package of claim 1, comprising a hanging feature to facilitate hanging of the package.

5. The package of claim 1, comprising an identifying feature to facilitate identifying contents of the package.

6. The package of claim 5, wherein the identifying feature comprises a barcode.

7. The package of claim 5, wherein the identifying feature comprises a color.

8. The package of claim 1, comprising a storage feature configured to provide storage for material associated with the medical device.

9. The package of claim 8, wherein the storage feature is configured to provide storage for lubricants or other liquids.

10. The package of claim 8, wherein the storage feature is configured to provide storage for at least one of a syringe or a $CO_2$ detector.

11. The package of claim 1, wherein the package is formed from polystyrene, polycarbonate, polypropylene, polyethylene terephthalate (PET), recycled polyethylene terephthalate (RPET), amorphous polyethylene terephalate, high density polyethylene (HDPE), low density polyethylene (LDPE), polyphenylene sulfide (RPS), polyvinyl chloride (PVC), polyvinylidene chloride (PVDC), or polyethylene terephthalate glycol (PETG).

12. The package of claim 1, wherein the package is comprised of transparent or semi-transparent material providing for visual inspection the contents of the package.

13. The package of claim 1, comprising an aperture configured to facilitate physical examination of the contents of the package.

14. The package of claim 1, wherein the package is formed from a pliable material configured to facilitate physical examination of contents of the package when a portion of the package surrounding the inflated region is depressed.

15. The package of claim 1, wherein the non-stretchable region is configured to provide support of the inflatable region at sterilization and shipping temperatures and pressures.

16. A shipping assembly, comprising:
a package; and
a medical device having an inflated region that is inflated within the package to a pressure of 20 to 75 cm $H_2O$; and
wherein the package comprises
a substantially non-stretchable region that substantially conforms to the shape of the inflated region of the medical device when the inflatable region is inflated to an inflated configuration comprising an internal cuff pressure sufficient to remove wrinkles from the cuff outside the patient without a constraint against a diameter of the cuff.

17. The shipping assembly of claim 16, wherein the package comprises feet configured to provide a support for the package.

18. The shipping assembly of claim 17, wherein the feet comprise features configured to interface with features of similar packages to provide for stacking of multiple packages.

19. The shipping assembly of claim 16, comprising a hanging feature to facilitate hanging of the shipping assembly.

20. The shipping assembly of claim 16, comprising an identifying feature to facilitate identifying the shipping assembly.

21. The shipping assembly of claim 20, wherein the identifying feature comprises a barcode.

22. The shipping assembly of claim 20, wherein the identifying feature comprises a color.

23. The shipping assembly of claim 16, comprising a storage feature configured to provide storage for material associated with the medical device.

24. The shipping assembly of claim 23, wherein the storage feature is configured to provide storage for lubricants or other liquids.

25. The shipping assembly of claim 23, wherein the storage feature is configured to provide storage for at least one of a syringe or a $CO_2$ detector.

26. The shipping assembly of claim 16, wherein the package is formed from polystyrene, polycarbonate, polypropylene, polyethylene terephthalate (PET), recycled polyethylene terephthalate (RPET), amorphous polyethylene terephalate, high density polyethylene (HDPE), low density polyethylene (LDPE), polyphenylene sulfide (RPS), polyvinyl chloride (PVC), polyvinylidene chloride (PVDC), or polyethylene terephthalate glycol (PETG).

27. The shipping assembly of claim 16, wherein the package is comprised of transparent or semi-transparent material providing for visual inspection of the medical device.

28. The shipping assembly of claim 16, wherein the package comprises an aperture configured to facilitate physical examination of the inflated region.

29. The shipping assembly of claim 16, wherein the package is formed from a pliable material configured to facilitate physical examination of the medical device inflated region when the package structure surrounding the inflatable region is depressed.

30. The shipping assembly of claim 16, wherein the non-stretchable region is configured to provide support of the inflated region at sterilization and shipping temperatures.

31. The shipping assembly of claim 16, wherein the medical device comprises an endotracheal tube.

32. The shipping assembly of claim 16, comprising an enclosure for the package and the medical device.

33. The shipping assembly of claim 16, wherein the package is configured to enclose regions other than the inflated region of the medical device.

34. A package for a medical device, comprising:
a medical device comprising a cuff, wherein the cuff is inflated to an inflated configuration comprising an internal cuff pressure sufficient to remove wrinkles from the cuff outside the patient without a constraint against a diameter of the cuff, wherein the internal cuff pressure is 20 to 75 cm $H_2O$; and
a package region that accommodates the cuff of the medical device when the cuff is in the inflated configuration.

35. The package of claim 34, wherein the package region is configured to provide support of the cuff at sterilization and shipping temperatures and pressures.

36. The package of claim 34, wherein the medical device comprises an endotracheal tube.

* * * * *